United States Patent
Aspinall

(10) Patent No.: US 9,778,147 B2
(45) Date of Patent: Oct. 3, 2017

(54) HEAT EXCHANGER TESTING DEVICE

(71) Applicant: Knew Value, LLC, Huffman, TX (US)

(72) Inventor: Laurin Joseph Aspinall, Huffman, TX (US)

(73) Assignee: Knew Value, LLC, Huffman, TX (US)

( * ) Notice: Subject to any disclaimer, the term of this patent is extended or adjusted under 35 U.S.C. 154(b) by 526 days.

(21) Appl. No.: 14/321,244

(22) Filed: Jul. 1, 2014

(65) Prior Publication Data

US 2015/0003495 A1    Jan. 1, 2015

Related U.S. Application Data

(60) Provisional application No. 61/841,643, filed on Jul. 1, 2013.

(51) Int. Cl.
*G01N 25/72* (2006.01)
*G01M 99/00* (2011.01)
*F28D 7/06* (2006.01)

(52) U.S. Cl.
CPC .......... *G01M 99/005* (2013.01); *F28D 7/06* (2013.01); *G01M 99/002* (2013.01); *G01M 99/008* (2013.01); *G01N 25/72* (2013.01); *F28F 2200/00* (2013.01)

(58) Field of Classification Search
CPC ......... G01K 17/00; G01K 17/06; G01K 17/08
USPC ...... 374/40, 44, 29, 30, 4, 5, 7, 43, 45, 147, 374/148, 39, 208
See application file for complete search history.

(56) References Cited

U.S. PATENT DOCUMENTS

| | | | |
|---|---|---|---|
| 3,921,436 A * | 11/1975 | Plegat | G01M 3/3227 73/40 |
| 4,044,605 A | 8/1977 | Bratthall | |
| 4,097,341 A * | 6/1978 | Schell | G01N 17/00 165/11.1 |
| 4,339,945 A | 7/1982 | Knudsen et al. | |
| 4,383,438 A | 5/1983 | Eaton | |

(Continued)

FOREIGN PATENT DOCUMENTS

| | | |
|---|---|---|
| DE | 29607030 | 4/1996 |
| DE | 19854773 | 11/1998 |

(Continued)

OTHER PUBLICATIONS

PCT International Search Report from corresponding International Application PCT/US2014/045078, dated Nov. 6, 2014.

(Continued)

*Primary Examiner* — Gail Kaplan Verbitsky
(74) *Attorney, Agent, or Firm* — Greer, Burns & Crain, Ltd.

(57) ABSTRACT

An apparatus and a process for testing fluid from a heat exchanger. A first fluid from a heat exchanger to be tested is passed through a test heat exchanger. A second fluid is circulated through the test heat exchanger with a pump. The second fluid is heated with a heater so that a temperature in the test heat exchanger can be controlled, for example, to so that conditions in the heat exchanger are close to the conditions in the heat exchanger. After a period of time, the test heat exchanger can be removed and inspected, tested, or both. Also, multiple test heat exchangers may be used to test various process conditions. Additionally, the test heat exchangers may include different materials to test various materials.

16 Claims, 9 Drawing Sheets

(56) References Cited

U.S. PATENT DOCUMENTS

| | | | | |
|---|---|---|---|---|
| 4,554,969 A | * | 11/1985 | Carnavos | F28D 7/106 165/154 |
| 4,686,853 A | | 8/1987 | Sugam et al. | |
| 4,813,270 A | * | 3/1989 | Baillie | G01F 1/74 374/33 |
| 4,906,307 A | * | 3/1990 | Fujiyoshi | B23K 35/3605 148/26 |
| 5,083,606 A | | 1/1992 | Brown et al. | |
| 5,215,704 A | * | 6/1993 | Hirota | F28F 19/00 374/39 |
| 5,353,653 A | * | 10/1994 | Watanabe | F22D 1/325 165/11.1 |
| 6,241,383 B1 | * | 6/2001 | Feller | G01K 7/16 374/135 |
| 6,499,876 B1 | * | 12/2002 | Baginksi | G01N 25/18 374/29 |
| 6,678,628 B2 | * | 1/2004 | Ryan | G01K 17/12 374/45 |
| 9,534,856 B2 | * | 1/2017 | Suzuki | F28F 21/04 |
| 2005/0160742 A1 | * | 7/2005 | Naaman | B60H 1/00478 62/3.2 |
| 2006/0021739 A1 | | 2/2006 | Young et al. | |
| 2006/0249020 A1 | * | 11/2006 | Tonkovich | B01D 53/04 95/115 |
| 2007/0209365 A1 | * | 9/2007 | Hamer | C09K 5/00 60/648 |
| 2007/0228113 A1 | * | 10/2007 | Dupree | F28D 9/0081 228/183 |
| 2008/0285616 A1 | * | 11/2008 | Nakanishi | G01N 3/60 374/57 |
| 2009/0087903 A1 | | 4/2009 | Belgrader et al. | |
| 2009/0173336 A1 | * | 7/2009 | Leifer | F24D 11/0257 126/617 |
| 2010/0036638 A1 | * | 2/2010 | Friedrich | F01K 13/02 702/136 |
| 2011/0283736 A1 | * | 11/2011 | Manabe | F25B 30/04 62/476 |
| 2013/0118706 A1 | * | 5/2013 | Kareh | G01N 25/18 165/11.1 |
| 2013/0340976 A1 | | 12/2013 | Kamiyama et al. | |
| 2014/0008035 A1 | * | 1/2014 | Patankar | F28F 27/00 165/11.1 |
| 2014/0021673 A1 | * | 1/2014 | Chen | F28D 15/00 269/289 R |
| 2014/0341256 A1 | * | 11/2014 | Azeem | G01K 1/16 374/165 |
| 2015/0101334 A1 | * | 4/2015 | Bond | F28F 9/013 60/728 |
| 2015/0168073 A1 | * | 6/2015 | Bugler, III | F24F 5/0035 165/60 |
| 2015/0226361 A1 | * | 8/2015 | Hernandez | E21B 36/001 165/279 |
| 2016/0126118 A1 | * | 5/2016 | Chen | F28D 15/00 165/80.5 |
| 2016/0146487 A1 | * | 5/2016 | Zywiak | F24F 11/001 374/45 |

FOREIGN PATENT DOCUMENTS

| | | |
|---|---|---|
| GB | 2292607 | 2/1996 |
| SU | 1778657 A1 * | 11/1992 |
| WO | 2012132587 | 4/2012 |

OTHER PUBLICATIONS

PCT Written Opinion of the International Searching Authority from corresponding International Application PCT/US2014/045078, dated Nov. 6, 2014.

European Search Report, dated Feb. 15, 2017 for Appl. No. 14820461.3-1557.

* cited by examiner

HEAT EXCHANGER TESTING DEVICE

CROSS-REFERENCES TO RELATED APPLICATIONS

This application claims priority to U.S. Provisional Patent Application No. 61/841,643 filed on Jul. 1, 2013, the entirety of which is incorporated herein.

BACKGROUND OF THE INVENTION

Heat exchangers often involve fluids flowing through conduits. The nature of the fluids passing through the heat exchangers and conduits, and the temperatures and other conditions present in the heat exchangers and conduits can lead to problems.

For example, various portions of the heat exchangers and conduits may become corroded as a result of the fluid, conditions or both. The corrosion can lead to leakage or breakage. Additionally, the heat exchangers and conduits may develop deposits as a result of materials in the fluid. The deposits may interfere with the flow of fluid through the heat exchangers and conduits and may also reduce the heat transfer capacity of same. Both of these problems are undesirable.

Many of these problems cannot be observed until after the heat exchanger has been online for some time. Furthermore, many of these problems can only be observed by removing and disassembling the heat exchanger and inspecting the conduits contained therein. The heat exchangers tend to be very large and can be quite costly. Additionally, removing the heat exchanger may require a process to shut down, which may impact a facility's production and output. Accordingly, it is crucial to avoid removing and disassembling a heat exchanger.

Therefore, it would be desirable to have an apparatus or process which allows for the materials of the conduits and the heat exchanger to be tested under nearly identical process conditions apart from the heat exchanger.

SUMMARY OF THE INVENTION

In one or more embodiments, the present invention provides a process and a device that can be placed inline with, or in a parallel line to, the fluid carrying conduits of the heat exchanger. The device can be subjected to the identical flow rates, temperatures, and other conditions of the heat exchangers that are used in the process (such as tube-and-shell heat exchangers) or other conduits. Accordingly, the testing device will be operated under nearly identical conditions as the heat exchangers in the plant or process. This will allow portions of the testing device to be disassembled and inspected for scale, corrosion and microbiological matter after a period of exposure time.

Therefore, in one aspect of the present invention, the invention provides a device for testing a heat exchanger configured to transfer heat to a first fluid, recover heat from the first fluid, or both. The device includes a test heat exchanger having a first inlet configured to receive the first fluid from the heat exchanger, a first outlet for the first fluid to the heat exchanger, a second inlet configured to receive a recirculating fluid, and, a second outlet for the recirculating fluid. The second outlet and the second inlet form a recirculation loop. The first fluid from the heat exchanger and the recirculating fluid are isolated fluidically. The device also includes a pump communicating with the test heat exchanger in the recirculation loop. Finally, the device includes a heater communicating with the test heat exchanger in the recirculation loop. The pump and the heater are configured to heat and circulate the recirculating fluid to adjust conditions in the test heat exchanger. The test heat exchanger, the pump and the heater are all disposed on a skid.

In at least one embodiment of the present invention, the test heat exchanger comprises a shell with at least one tube inside of the shell. Accordingly, it is contemplated that the first fluid from the heat exchanger flows inside of the at least one tube of the test heat exchanger and the recirculating fluid flows outside of the at least one tube. Alternatively, it is contemplated that the recirculating fluid flows inside of the at least one tube of the test heat exchanger and the first fluid from the heat exchanger flows outside of the at least one tube of the test heat exchanger.

In some embodiments of the present invention, the device includes a second test heat exchanger. The second test heat exchanger includes a first inlet configured to receive the first fluid from the heat exchanger, a first outlet for the first fluid from the heat exchanger, a second inlet configured to receive the recirculating fluid, and, a second outlet for the recirculating fluid. The first fluid from the heat exchanger and the recirculating fluid are isolated fluidically in the second test heat exchanger. It is contemplated that the first test heat exchanger comprises an inner tube in an outer tube and the second test heat exchanger comprises an inner tube in an outer tube. It is further contemplated that the inner tube of the first test heat exchanger comprises a first material, and the inner tube of the second test heat exchanger comprises a second material different than the first material.

In at least one embodiment of the present invention, the device includes at least one probe disposed in a conduit for the first fluid from the first heat exchanger, the recirculating fluid, or both.

In one or more embodiments of the present invention, an exterior portion of the test heat exchanger is semitransparent.

In another aspect of the present invention, the invention provides a process for testing a fluid from a conduit which includes: passing a portion of a first fluid from a heat exchanger to a test heat exchanger; circulating a second fluid through the test heat exchanger with a pump; and, heating the second fluid in a heater in order to control a temperature of the test heat exchanger, wherein the first fluid and second fluid are isolated fluidically.

In at least one embodiment, the test heat exchanger comprises a shell with at least one tube inside of the shell. Accordingly, it is contemplated that the process further includes passing the first fluid through the at least one tube of the test heat exchanger, and, passing the second fluid through the shell of the test heat exchanger and outside of the at least one tube of the test heat exchanger. Alternatively, it is contemplated that the process further includes circulating the second fluid through the at least one tube of the heat exchanger, and, passing the first fluid through the shell of the test heat exchanger and outside of the at least one tube of the test heat exchanger.

In at least one embodiment, monitoring a flow rate of at least one of the first fluid and the second fluid.

In one or more embodiments of the present invention, the process also includes passing at least a portion of the first fluid through a second test heat exchanger, circulating at least a portion of the second fluid through the second test heat exchanger with the pump, wherein the first fluid and second fluid are isolated fluidically in the second test heat exchanger, and, heating the second fluid in the heater to control a temperature of the second test heat exchanger. It is contemplated that the first test heat exchanger comprises an inner tube in an outer tube and the second test heat exchanger comprises an inner tube in an outer tube. It is further contemplated that the inner tube of the first test heat exchanger comprises a first material, and the inner tube of the second test heat exchanger comprises a second material different than the first material.

In some embodiments of the present invention, the process includes removing the test heat exchanger from the process. It is further contemplated that the process includes testing at least a portion of the test heat exchanger which had received the first fluid from the heat exchanger.

In at least one embodiment of the present invention, an exterior portion of the test heat exchanger is semitransparent.

These and other embodiments and aspects of the present invention will be appreciated by those of ordinary skill in the art based upon the following description of some of the embodiments and aspects of the present invention.

BRIEF DESCRIPTION OF THE DRAWINGS

The figures in the appended drawing will make it possible to understand how the invention can be produced. In these figures, similar reference numbers denote similar elements.

DETAILED DESCRIPTION OF THE PREFERRED EMBODIMENTS

Figure 1:
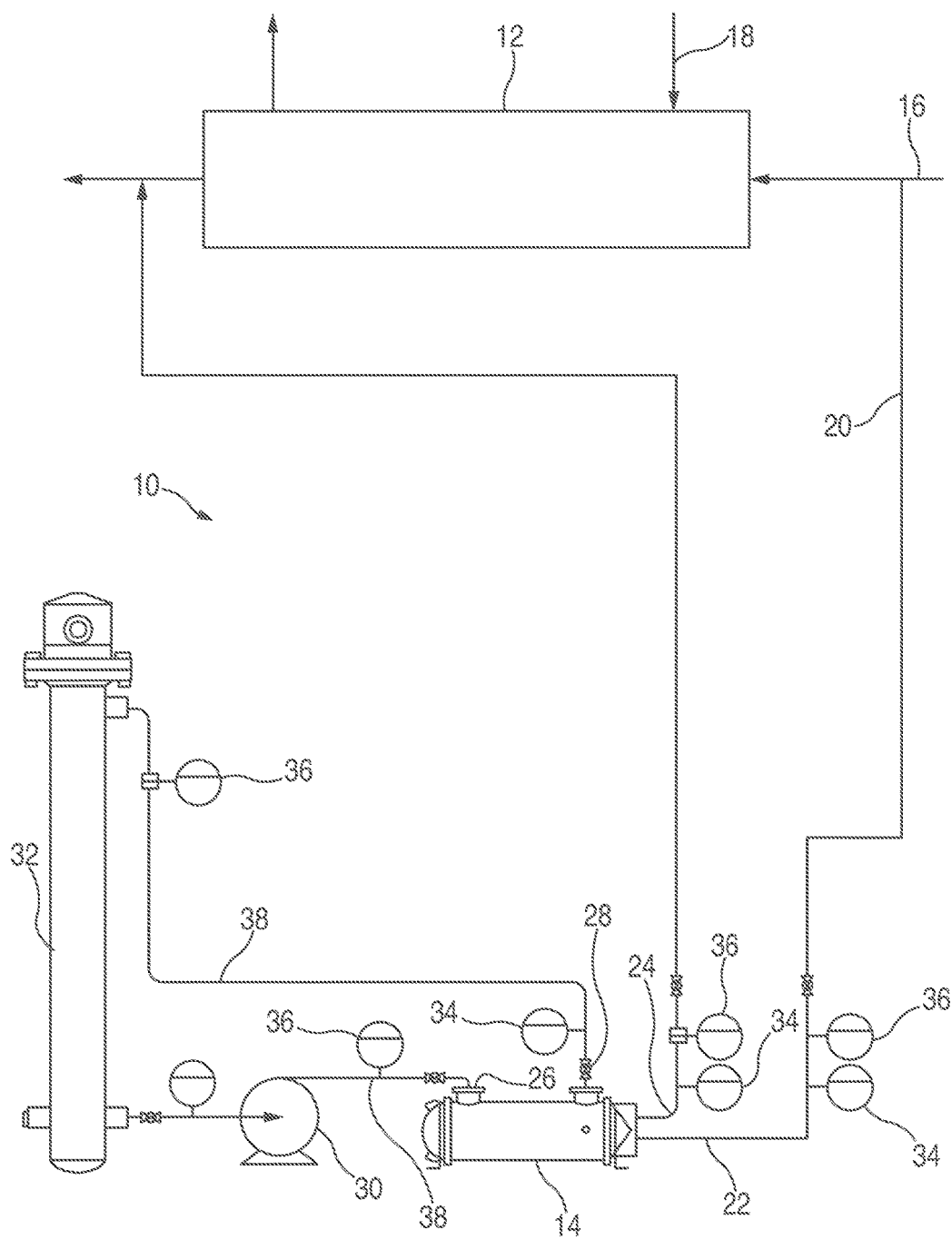
FIG. 1 is a schematic view of a device according to an embodiment of the present invention.

With reference to FIG. 1, a device 10 according to one or more embodiments of the present invention is shown which include a first heat exchanger 12 and a test heat exchanger 14. The first heat exchanger 12 receives a first fluid, for example via a line 16, and recovers heat from the first fluid, or passes heat to the first fluid, or both. Typically, the first heat exchanger 12 also receives another fluid, for example, via a line 18, which can supply heat to the first fluid or receive heat from the first fluid. These heat exchangers 12 are known.

In order to test the materials of the first heat exchanger 12, a portion of the first fluid is passed, via a line 20, to the test heat exchanger 14. Accordingly, the test heat exchanger 14 has an inlet 22 for the first fluid and an outlet 24 to return the first fluid to the first heat exchanger 12. The first fluid may be combined with fluid exiting the first heat exchanger 12, and it would still be considered returning the first fluid to the first heat exchanger 12.

As shown in FIG. 1, the test heat exchanger 14 also has an inlet 26 for a recirculating fluid and an outlet 28 for the recirculating fluid. Within the test heat exchanger 14, the first fluid and the recirculating fluid do not come into fluid contact (i.e., the two are isolated fluidically). In one embodiment of the present invention the recirculating fluid is glycol, however any other such fluids, such as water, may be used.

The recirculating fluid is circulated into and out of the test heat exchanger 14 via a pump 30 in a recirculation loop. In order to adjust the temperature of the recirculating fluid, the device 10 includes a heater 32. The heater 32 may be used to adjust the temperature of the recirculating fluid, which in turn will adjust the temperature in the test heat exchanger 14 to have similar operating conditions to the first heat exchanger 12.

Appropriate temperature sensors 34 are used to maintain the test heat exchanger 14 at a temperature approximately equal to the temperatures of the first heat exchanger 12. Additionally, flow meters 36 are provided in at least one line 38 to allow for appropriate calculations of erosion and scale deposit which may be extrapolated from the test period of operation of the test heat exchanger 14.

The test heat exchanger 14 of the device 10 can be operated for a predetermined period of time. For example, the device 10 can be operated for an amount of time that is sufficient to determine corrosion levels in the first heat exchanger 12 by extrapolating the data from the test heat exchanger 14. In order to view the corrosion, mineral deposits, or other problems that may arise, the test heat exchanger 14 can be removed from the device 10 and opened for visual inspection. If needed, one or more portions of the test heat exchanger 14 can be destructively tested.

Figure 2A:
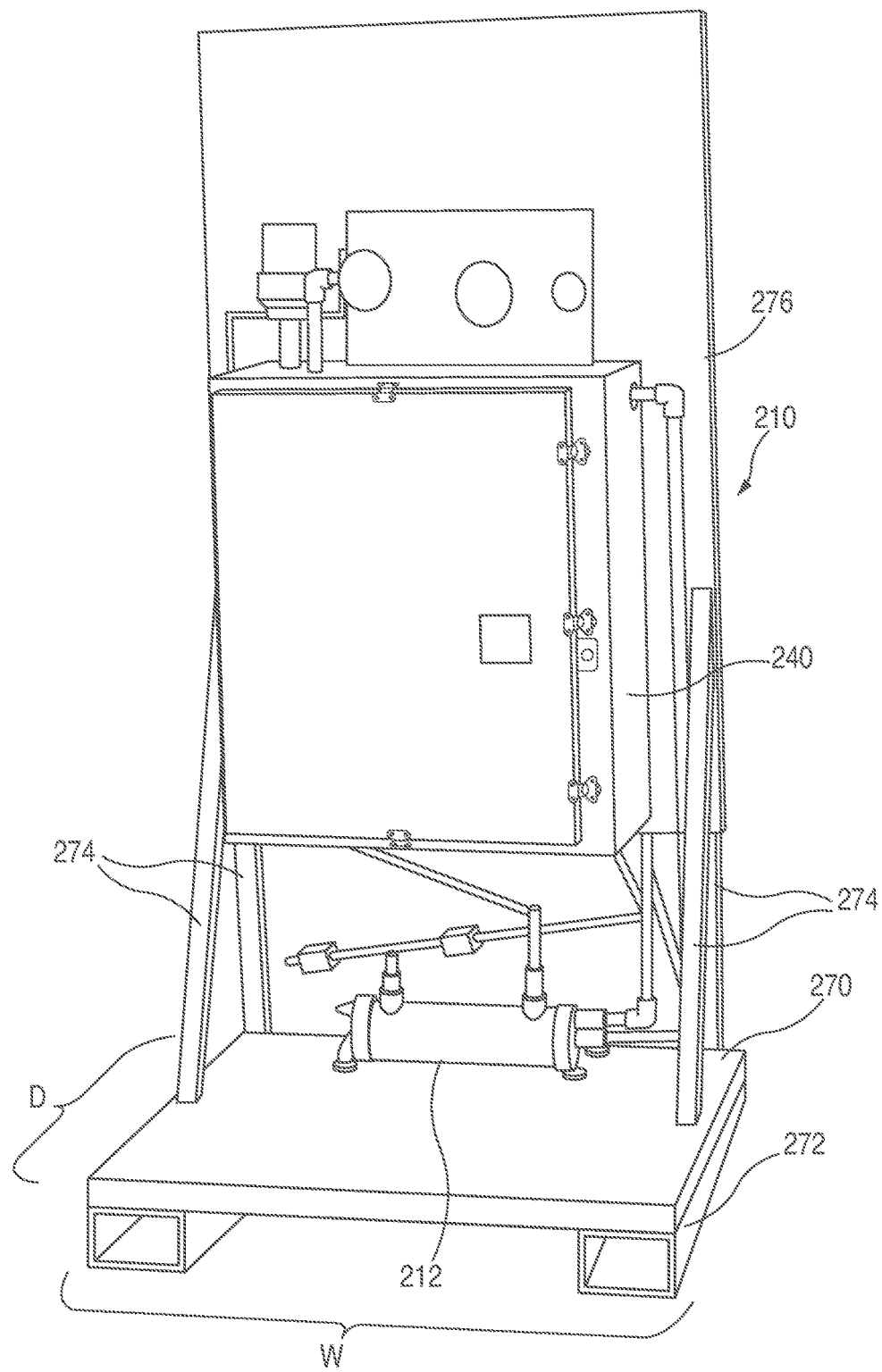
FIG. 2A is front perspective view of a device according to one or more embodiments of the present invention.
Figure 2B:
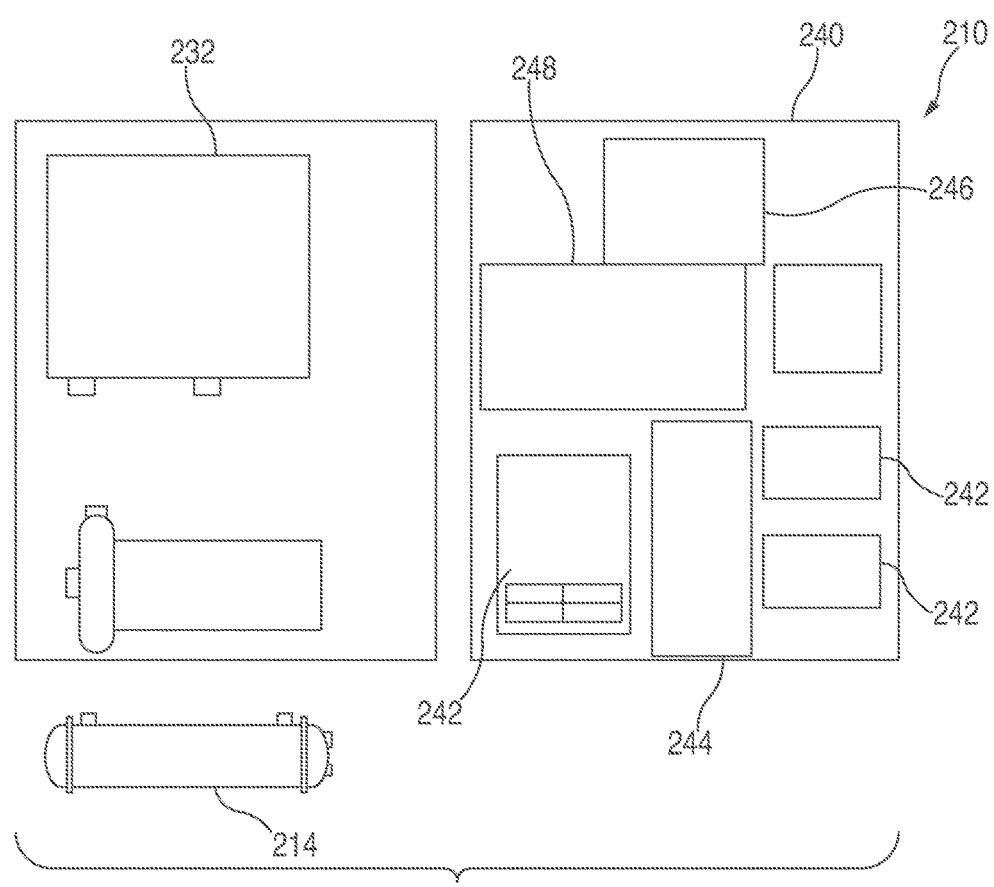
FIG. 2B is a schematic view of a portion of the device shown in FIG. 2A.

Another embodiment of the present invention is shown in FIGS. 2A and 2B in which components which are similar to the ones described above, have similar reference numerals with the exception of a preceding "2."

As shown in this embodiment, the device 210 includes a test heat exchanger 212 and a housing 240 mounted on a skid 270. Although not shown, a pump and a heater are disposed inside of the housing 240 (see FIG. 2B, below). The skid 270, or movable platform, includes a base 272, supports 274, and a backing 276. The base 274 of the skid 270 has a width W of approximately 0.91 meters (36 inches) and a depth D of approximately 1.1 (42 inches). For example, the base 274 of the skid 270 may be sized so that the device 210, including the test heat exchanger 212, can be moved with a pallet jack or other similar devices for moving pallets. Such a device 210 can be easily placed near operating heat exchangers and placed online for the testing period. Once the testing period is completed, the device 210 can be taken offline, inspected, and, if desired, moved to another location for testing.

As shown in FIG. 2B, a potential equipment layout arrangement for the housing 240 according to one embodiment includes a pump 230 typically driven by a motor, and a heater 232. Various electrical components of the device are shown as also being contained in the housing 240 including various circuit breakers 242, transformers 244, switches, input/output devices 246, and instrumentation 248. The input/output devices 246 can be, for example, a touch screen which displays information associated with the temperature sensors 32 or flow meters 36. See, FIG. 1. Additionally, the input/output devices 246 can allow for control of the heater 232 to adjust the temperature or adjust valves (discussed below) to control the flow of fluids in the device.

Figure 3A:
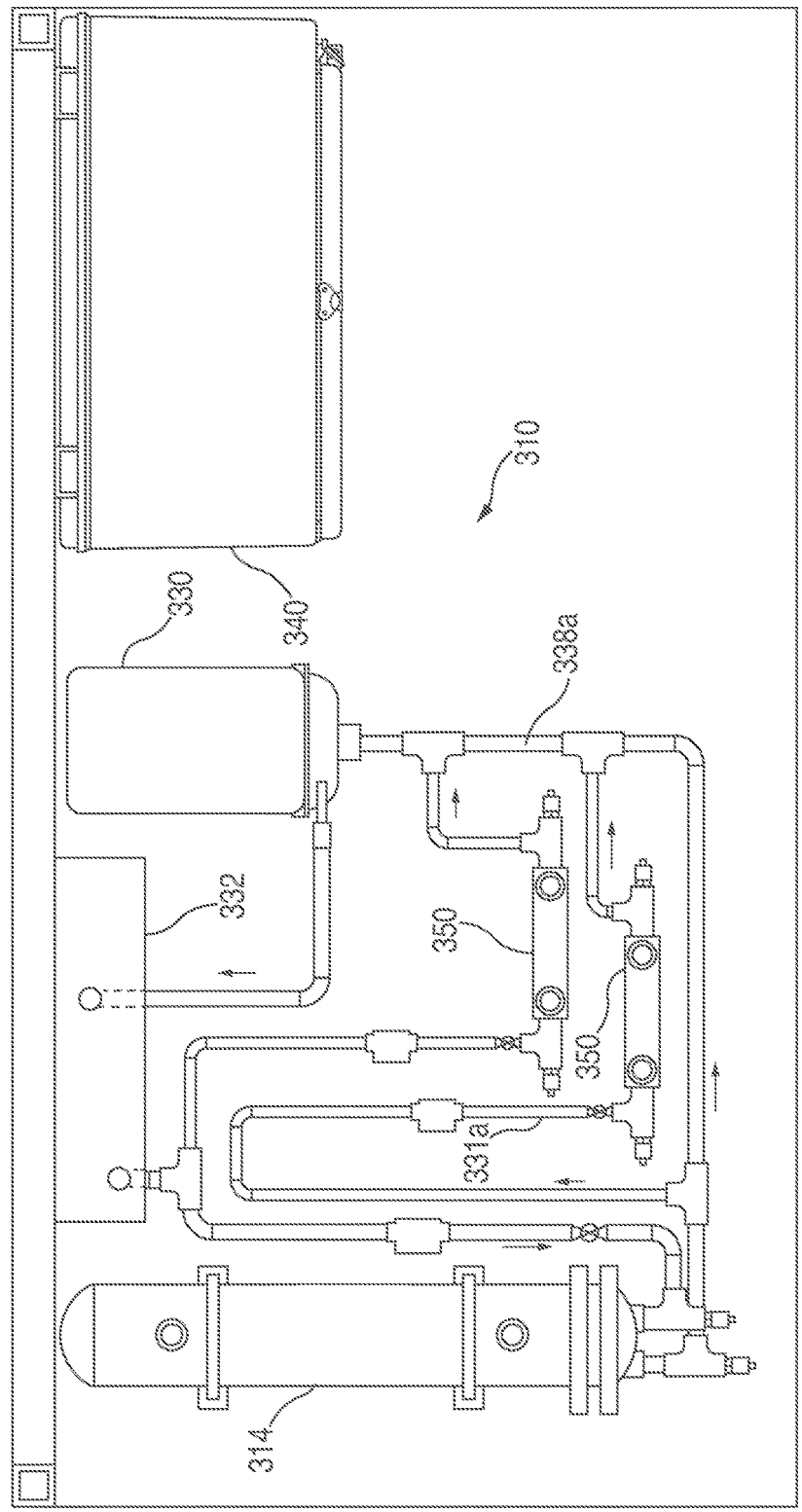
FIG. 3A is a top view of a device according to an embodiment of the present invention showing conduit lines for a recirculating fluid.
Figure 3B:
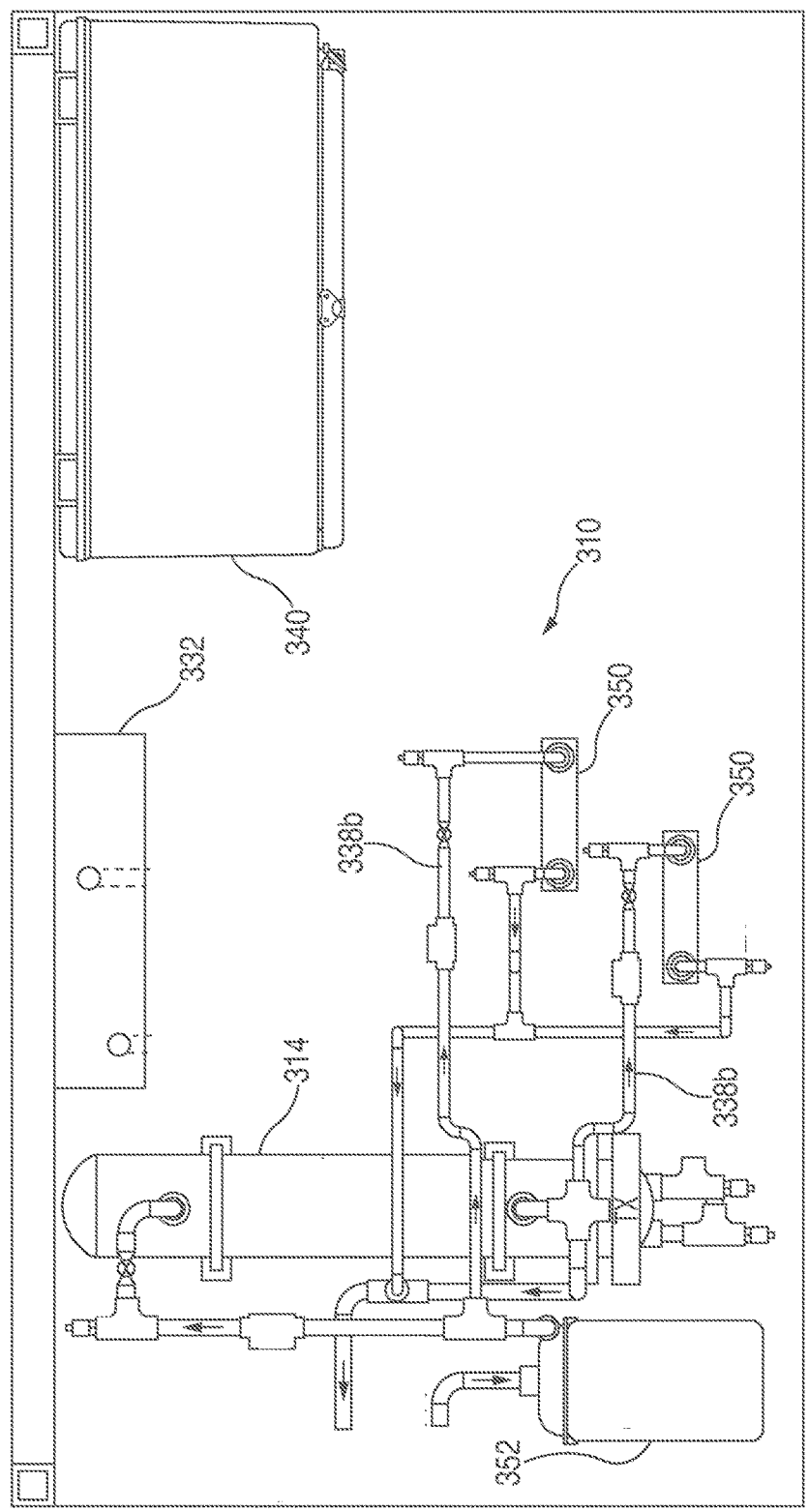
FIG. 3B is a top view of the device shown in FIG. 3A showing conduit lines for a fluid from a heat exchanger.

Another embodiment of the present invention is shown in FIGS. 3A and 3B in which components which are similar to the ones described above, have similar reference numerals with the exception of a preceding "3."

As shown in this embodiment, the device 310 includes one or more testing probes 350 disposed in, for example, conduits 338a for the second fluid. In a preferred embodiment, the testing probe 350 is capable of testing both the first fluid and the recirculating fluid.

In FIG. 3A, for example, the probe 350 is disposed within a conduit 338a for the recirculating fluid. As can be seen in FIG. 3B, the probe 350 also receives a portion of the first fluid via conduits 338b. The probes 350 can provide, for example, pH values, ionic data, or other data about the first fluid or the recirculating fluid.

Additionally, as can be seen in FIG. 3B, in this embodiment, the device 310 includes a second pump 352. The second pump 352 moves the first fluid throughout the device 310, including the probes 350, in order to avoid any pressure drop.

Figure 4:
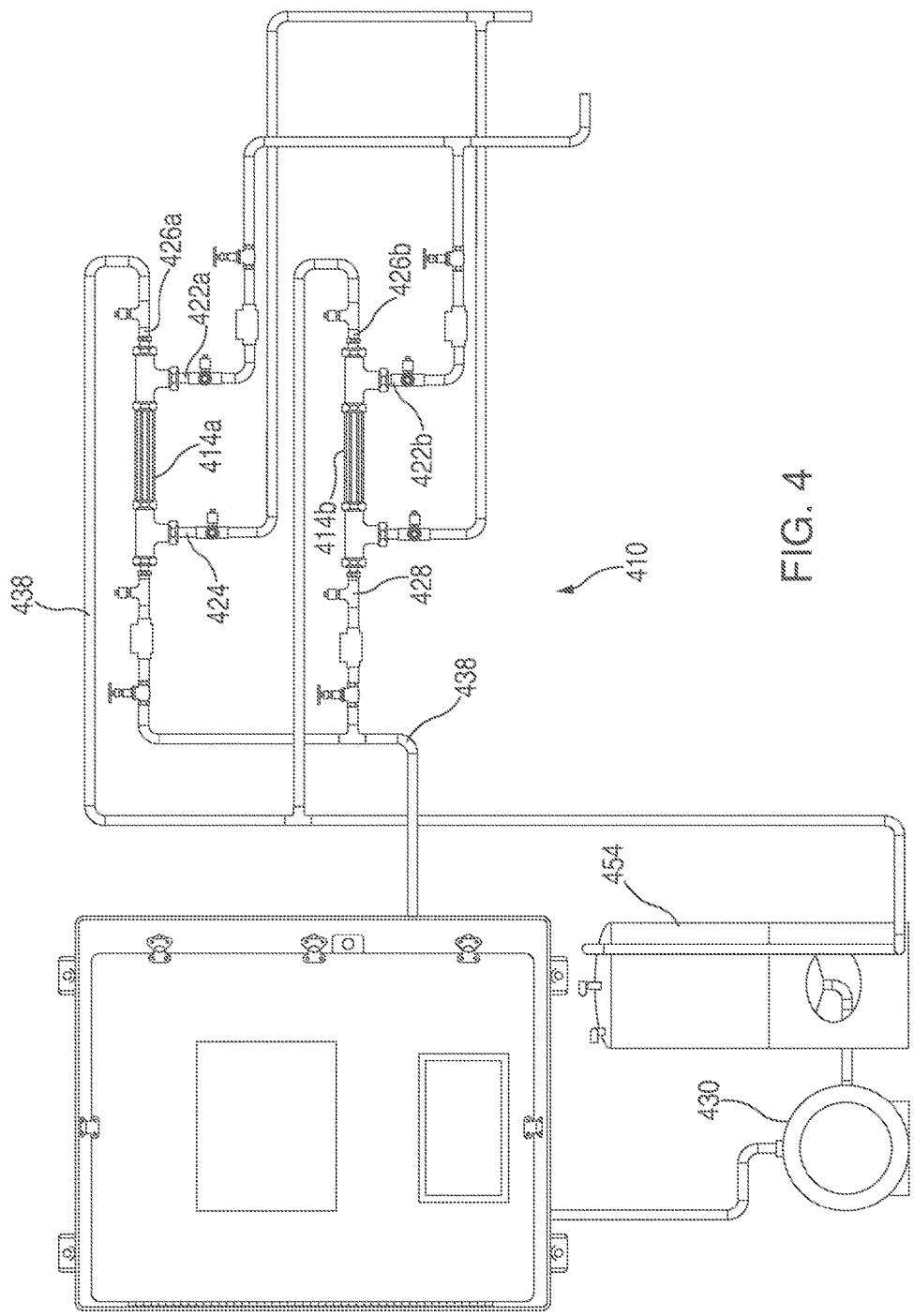
FIG. 4 is a front view of a device according to an embodiment of the present invention.

Accordingly, another embodiment is shown in FIG. 4 in which components which are similar to the ones described above, have similar reference numerals with the exception of a preceding "4."

As depicted in FIG. 4, a device 410 includes two test heat exchangers 414a, 414b which are arranged in parallel. It is also contemplated that the test heat exchangers 414a, 414b could be arranged in series. Each test heat exchanger 414a, 414b receives a portion of the first fluid via inlets 422a, 422b and a portion of the recirculating fluid via inlets 426a, 426b. By utilizing more than one test heat exchanger 414a, 414b, different materials, such as metals, metal alloys, or other materials typically used or conditions can be evaluated at the same time.

Additionally, as shown in FIG. 4, this embodiment of the device 410 includes a tank 452 which operates as a reservoir for recirculating fluid. If needed, additional fluid can be withdrawn from the tank 452.

Figure 5:
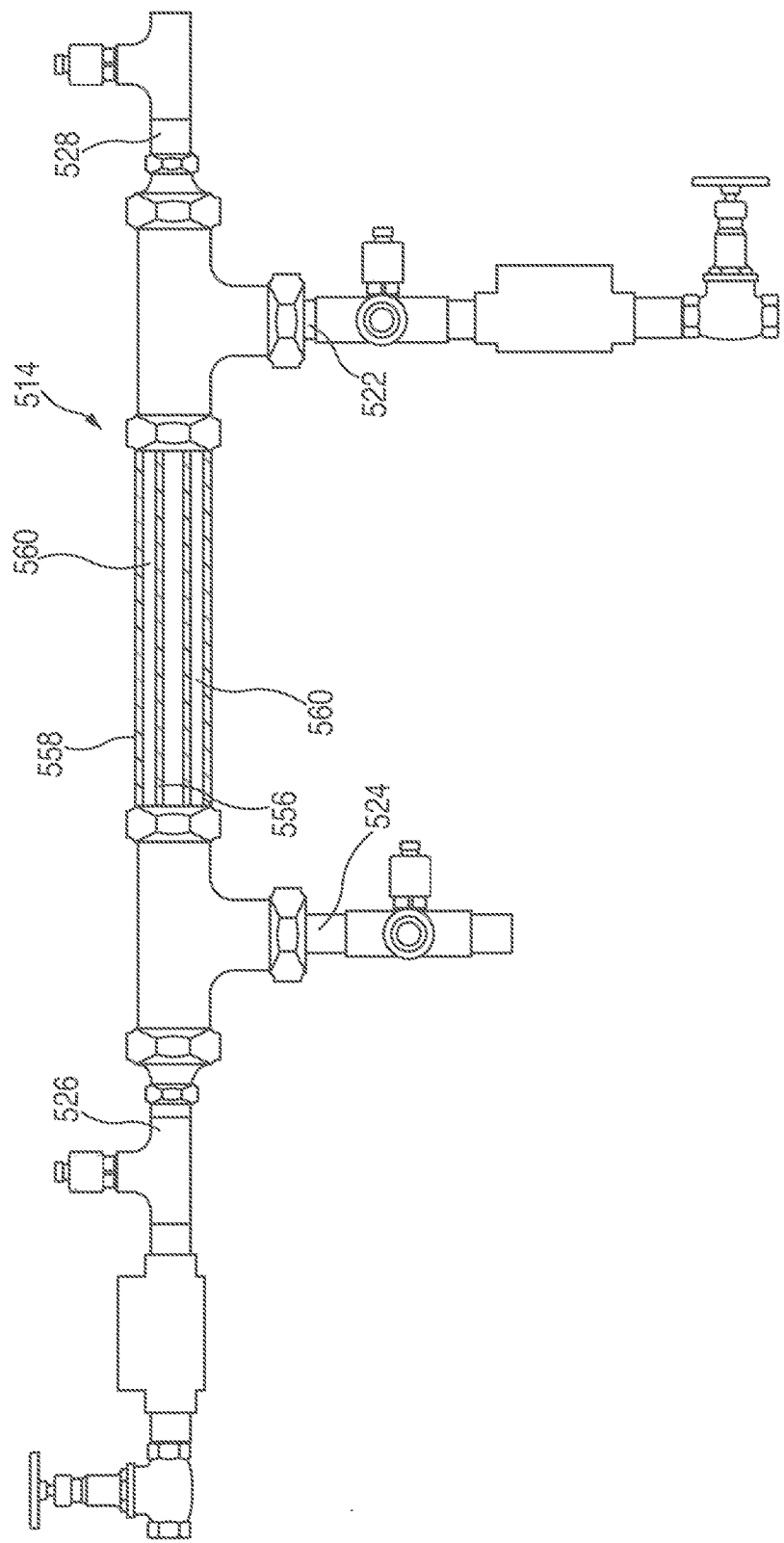
FIG. 5 is a side partial cutaway view of a heat exchanger used in one or more embodiments of the present invention.
Figure 6:
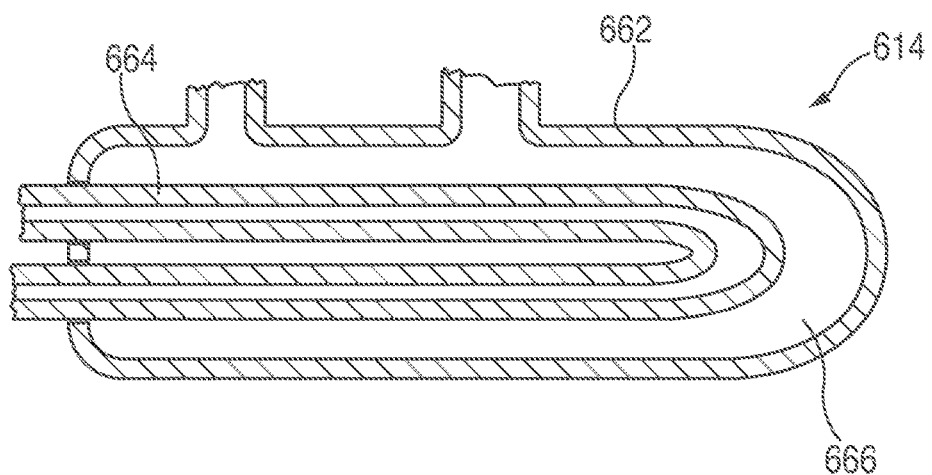
FIG. 6 is a side cutaway view of another heat exchanger used in one or more embodiments of the present invention.

FIGS. 5 and 6 depicted various designs for the test heat exchangers that may be utilized in the various embodiments of the present invention.

In FIG. 5, for example, a test heat exchanger 514 is shown which comprises a tube-in-tube design. The tube-in-tube test heat exchanger 514 includes an inner tube 556 and an outer tube 558. One fluid flows inside of the inner tube 556, and the second fluid flows in a space 560 between the inner tube 556 and the outer tube 558. It is contemplated that a portion of a heat exchanger 514, for example the outer tube 558, is at least semi-transparent to allow for visual inspection while the device is operating.

As shown for example in FIG. 6, a test heat exchanger 614 comprises a tube-and-shell heat exchanger 614. The tube-and-shell heat exchanger 614 comprises an outer shell 662 with at least one tube 664 inside of the shell 662. A first fluid flows in the at least one tube 664, while the second flows in a space 666 between the shell 662 and the at least one tube 664.

For example, the recirculated fluid may flow in the space 666 between the shell 662 and the at least one tube 664, while the first fluid flows with the at least one tube 664. Alternately, the recirculated fluid may flow through the at least one tube 664 and the first fluid may flow in the space 666 between the shell 662 and the at least one tube 664.

As will be appreciated other designs for the test heat exchanger may be used in which the test heat exchanger allows for the conditions of the test heat exchanger to reproduce the conditions of the heat exchanger.

Figure 7:
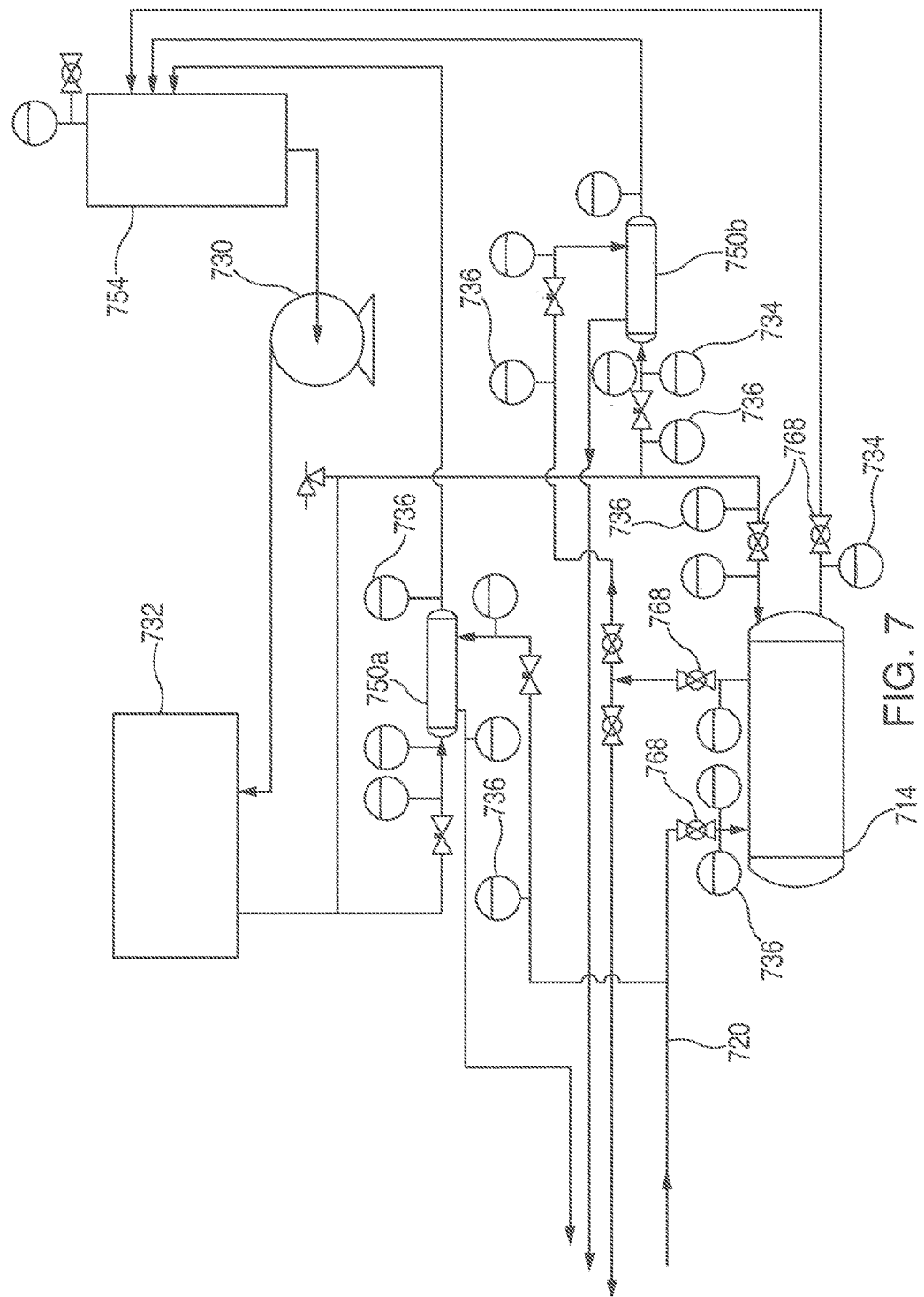
FIG. 7 is a process flow diagram according to one or more embodiments of the present invention.

With reference to FIG. 7, in which components which are similar to the ones described above, have similar reference numerals with the exception of a preceding "7," an exemplary process according to the present invention will be described.

A portion of the first fluid which is passed to a heat exchanger is passed via a line 720 to at least one test heat exchanger 714. The first fluid in line 720 preferably is a slip stream of a conduit passing the first fluid into the heat exchanger, although other configurations may also be employed. A portion of the first fluid may also be passed to a first probe 750a to obtain, for example, electrochemical or other conditions of the first fluid.

The first fluid is passed through test heat exchanger 714. Upon exiting the test heat exchanger 714, the first fluid may be passed back to the heat exchanger. It is contemplated that a portion of the first fluid after it exits the test heat exchanger 714 may be passed to a second probe 750b to obtain, again, for example, electrochemical or other conditions of the first fluid. The first fluid could be returned upstream to the heat exchanger or downstream of the heat exchanger.

In addition to the first fluid, the test heat exchanger 714 receives a recirculating fluid that is passed in a recirculation loop via a pump 730. Accordingly, recirculating fluid may be passed from a tank 754 to a heater 732 to obtain a desired temperature. Once the recirculating fluid has been heated, the recirculating fluid is passed to the test heat exchanger 714. After passing through the test heat exchanger 714, the recirculating fluid may be returned to the tank 754. A portion of the recirculating fluid exiting the test heat exchanger 714 may also be passed to each of the probes 750a, 750b.

Flow meters 736 and temperature sensors 734 may be used to monitor the flow rates and temperatures of the fluids at various positions in the process. Valves 768 and the heater 732 can be used to adjust the temperature(s) and flow rate(s) into and out of the test heat exchanger 714 so that it is equivalent to the operating conditions of the heat exchanger. Additionally, the temperature(s) and flow rate(s) can be adjusted to allow for the testing of different operating conditions in each test heat exchanger to allow for simultaneous testing. Furthermore, in devices and process with multiple heat exchangers, the different heat exchangers can include different materials, different operating conditions or both, to allow the testing of multiple conditions and materials at the same time.

After an amount of time that is preferably predetermined to be sufficient, any of the test heat exchangers can be taken offline and inspected at a fraction of the cost of the heat exchanger. Further, there is minimal, if any, impact on the heat exchanger operations as it can continue to be operated while the test heat exchanger is being inspected and potentially subjected to destructive testing. thus in addition to avoiding the destruction of the expense heat exchanger, the devices and processes of the present invention allow the process using the heat exchangers to continue operations while the teste heat exchanger is removed, inspected and tested.

As is apparent from the foregoing specification, the invention is susceptible of being embodied with various alterations and modifications which may differ particularly from those that have been described in the preceding specification and description. It should be understood that I wish to embody within the scope of the patent warranted hereon all such modifications as reasonably and properly come within the scope of my contribution to the art.

The invention claimed is:

1. A process for monitoring a heat exchanger configured to transfer heat between a first fluid and second fluid, the process comprising:
   passing the first fluid to the heat exchanger to change a temperature of the second fluid;
   passing a portion of the first fluid to a first test heat exchanger, wherein the first test heat exchanger comprises at least one inner tube;
   circulating a heat transfer fluid in a recirculation loop, wherein the recirculation loop includes the first test heat exchanger;
   heating the heat transfer fluid in order to control an internal temperature of the test heat exchanger, wherein the first fluid and heat transfer fluid are isolated fluidically in the recirculation loop;
   circulating a second portion of the first fluid through a second test heat exchanger, wherein the second heat exchanger comprises a shell with at least one inner tube inside of the shell, wherein the first fluid and the heat transfer fluid are isolated fluidically in the second test heat exchanger, wherein the second test heat exchanger is in the recirculation loop, and wherein a temperature of the second test heat exchanger is controlled with the heat transfer fluid; and,
   determining a condition of the heat exchanger by inspecting at least one of the first test heat exchanger and the second test heat exchanger.

2. The process of claim 1 wherein the first test heat exchanger further comprises a shell with the at least one tube inside of the shell.

3. The process of claim 2 further comprising:
   passing the first fluid through the at least one inner tube of the first test heat exchanger; and,
   passing the heat transfer fluid through the shell of the first test heat exchanger and outside of the at least one inner tube of the first test heat exchanger.

4. The process of claim 2 further comprising:
   circulating the heat transfer fluid through the at least one inner tube of the first test heat exchanger; and,
   passing the first fluid through the shell of the first test heat exchanger and outside of the at least one inner tube of the first test heat exchanger.

5. The process of claim 2 further comprising:
   monitoring a flow rate of at least one of the first fluid and the heat transfer fluid, and wherein the condition of the heat exchanger is further determined based upon the flow rate of at least one of the process fluid and the second heat transfer fluid.

6. The process of claim 1 wherein the first test heat exchanger comprises an outer tube with the at least one inner tube disposed within the outer tube and the second test heat exchanger comprises an outer tube with the at least one inner tube disposed within the outer tube.

7. The process of claim 6 wherein the at least one inner tube of the first test heat exchanger comprises a first material, and the at least one inner tube of the second test heat exchanger comprises a second material different than the first material.

8. The process of claim 1 further comprising:
   taking at least one of the first test heat exchanger and the second test heat exchanger offline.

9. The process of claim 1, wherein the shell of the test heat exchanger is at least semi-transparent.

10. A process for monitoring a heat exchanger that is configured to a transfer heat between a first fluid and a second fluid, the process comprising:
    passing a portion of the first fluid to a first test heat exchanger;
    passing a second portion of the first fluid through a second test heat exchanger;
    circulating a heat transfer fluid through the first test heat exchanger and through the second test heat exchanger with a pump;
    fluidically isolating the first fluid and heat transfer fluid;
    heating the heat transfer fluid in order to control an internal temperature of the first test heat exchanger and in order to control an internal temperature of the second test heat exchanger; and,
    determining a condition of the heat exchanger by inspecting at least one of the first test heat exchanger and the second heat exchanger,
    wherein the first test heat exchanger comprises an outer tube with at least one inner tube disposed within the outer tube and the second test heat exchanger comprises an outer tube with at least one inner tube disposed within the outer tube, and
    wherein a material of the at least one inner tube of the first test exchanger is different from a material of the at least one inner tube of the second test heat exchanger.

11. The process of claim 10 wherein the outer tube of the first test heat exchanger is at least semitransparent.

12. The process of claim 10 further comprising:
    passing the first fluid to the heat exchanger to remove heat, within the heat exchanger, from the second fluid.

13. A process for monitoring a heat exchanger, the process comprising:
    passing a first fluid to a heat exchanger to remove heat from a second fluid;
    passing a portion of the first fluid through a first test heat exchanger;
    recirculating a heat transfer fluid through the first test heat exchanger;
    fluidically isolating the first fluid and the heat transfer fluid;
    heating the heat transfer fluid in order to control an internal temperature of the first test heat exchanger; and,
    determining a condition of the heat exchanger by inspecting the first test heat exchanger,
    wherein the first test heat exchanger comprises an outer tube with at least one inner tube disposed within the outer tube, and
    wherein the outer tube of the first test heat exchanger is at least semitransparent.

14. The process of claim 13 further comprising:
    monitoring the at least one inner tube for corrosion while the first fluid and the heat transfer fluid are being passed through the first test heat exchanger.

15. The process of claim 14, wherein the first fluid is passed through a space between the outer tube and the at least one inner tube, and wherein the heat transfer fluid is passed through the at least one inner tube.

16. The process of claim 13, wherein at least one of the first fluid and the heat transfer fluid is water.

* * * * *